United States Patent [19]

Breda et al.

[11] Patent Number: 4,501,491

[45] Date of Patent: Feb. 26, 1985

[54] DEVICE FOR OPTICAL INDICATION OF THE PHENOMENA OF COAGULATION OF BLOOD, CONCENTRATION AND AGGREGATION OF BLOOD PLATELETS, OR THE LIKE

[75] Inventors: Enzo Breda; Alfredo Ciotti, both of Udine, Italy

[73] Assignee: SALUS Ricerca e Sviluppo di CROCE' Dr. Francesco & C. Snc, Udine, Italy

[21] Appl. No.: 356,299

[22] Filed: Mar. 10, 1982

[30] Foreign Application Priority Data

Mar. 23, 1981 [IT] Italy .................................. 83349 A/81

[51] Int. Cl.³ ...................... G01N 33/48; G01N 21/13
[52] U.S. Cl. ...................................... 356/39; 356/440; 422/65
[58] Field of Search ...................... 356/39, 40, 41, 244, 356/440; 422/65; 250/576

[56] References Cited

U.S. PATENT DOCUMENTS

| Re. 28,800 | 5/1976 | Acker et al. |
|---|---|---|
| 2,959,665 | 11/1960 | Rhees . |
| 3,272,240 | 9/1966 | Roth . |
| 3,533,744 | 10/1970 | Unger .................. 356/39 X |
| 3,544,225 | 12/1970 | Wattenburg et al. ............ 356/39 X |
| 3,767,364 | 10/1973 | Ritchie et al. . |
| 3,847,482 | 11/1974 | Sokol et al. ..................... 356/40 |
| 3,963,355 | 6/1976 | Aldridge, Jr. et al. ......... 356/244 X |
| 4,125,327 | 11/1978 | Margolis . |
| 4,147,250 | 4/1979 | Schulz . |

FOREIGN PATENT DOCUMENTS

| 1921302 | 11/1969 | Fed. Rep. of Germany . |
|---|---|---|
| 2408214 | 2/1974 | Fed. Rep. of Germany . |
| 2383444 | 10/1978 | France . |
| 2030535 | 4/1980 | United Kingdom . |

Primary Examiner—Vincent P. McGraw
Attorney, Agent, or Firm—Stevens, Davis, Miller & Mosher

[57] ABSTRACT

Indicator device to study the phenomena of blood coagulation, concentration and aggregation of blood platelets and the like including support means (14) bearing test tubes (13) equipped in a plurality of upright hollows (114) provided with very narrow crosswise through holes (214), conveyor means (15) and withdrawal means (17) for said support means (14) to and from an indicator station (11) provided with loading discharging means (16) and including means (27) generating light, photosensor means (28), stirring means (29) and thermostat heating means characterized by the fact that said indicator station (11) comprises a length-wise lodgement (111) for said support means (14) bearing test tubes, whereby said lodgement (111) is equipped with a plurality of holes (226) to convey optical rays and said holes (226) correspond in number, position and advantageously also in diameter to the plurality of said crosswise holes (2147) provided in said support means (14) bearing test tubes positioned in an intermediate position in relation to said conveyor holes (226), and possibly comprising electronic means to coordinate and regulate the working of the conveyor means (15), withdrawal means (17), loading/discharging means (16) and means (18) injecting reagents.

5 Claims, 3 Drawing Figures

DEVICE FOR OPTICAL INDICATION OF THE PHENOMENA OF COAGULATION OF BLOOD, CONCENTRATION AND AGGREGATION OF BLOOD PLATELETS, OR THE LIKE

This invention relates to a device for optical indication of the phenomena of coagulation of blood, concentration and aggregation of blood platelets, or like phenomena relating to the activity of lyses such as fibrinolyses.

More particularly, the invention relates to an optical device to indicate the phenomena of variation of optical density which are found in the various tests conducted according to present analytical procedures relating to blood vessels, such as the concentration and aggregation of blood platelets, calculation of coagulation times and like happenings which can be displayed by measuring the opacity of the plasma or mixture of plasma with suitable reagents under controlled temperature and stirring conditions.

It is known that the passage of light through a sample of plasma has been employed as a means for determining, for example, the concentration of blood platelets and for monitoring the aggregation of the platelets in the plasma as well as for showing the formation of fibrin. All these phenomena are generally accompanied by a variation in the opacity of the plasma being examined.

The intensity of the light transmitted through the sample and received by a photosensor element located downstream from the sample is linked directly to the opacity of the sample and provides information concerning the phenomenon being investigated.

It is known that the attenuation of a ray of light passing through a sample is expressed as optical density and is indicated by the opacity of the plasma.

In fact, when the concentration of blood platelets in the plasma is being determined, it is known that the optical density increases with an increase in their concentration.

Furthermore, it is known that the attenuation of the ray of light passing through the plasma is caused either by absorption or by dispersion of the ray by the platelets or other particles present or forming in the plasma.

It has been confirmed that attenuation by absorption depends substantially on the wave length of the light transmitted, whereas dispersion depends on the optical geometry of the detector devices and of the ray of light itself.

For instance, it is known that the shorter the path of the ray of light through the sample, the more linear the ratio between the concentration of platelets and the optical density of the light. In fact it seems that, where light dispersion is dominant the optical density is proportional to the length of the path of the ray through the sample.

Moreover, it has already been shown that the linear nature of the ratio between optical density and concentration depends both on the fields of view of the photosensor and on the distance between the photosensor and the test tube of the plasma.

Optical indicator devices for the analysis of blood are known which employ a ray of light passing through the sample, the ray being detected by a photosensor able to generate an electrical signal which is proportional to the intensity of the light detected and which indicates the optical density of the sample.

GB Pat. No. 1,302,396 proposes a device for researching the fibrinolytic activity of blood, whereby the device comprises a plate to hold a substrate of reagent and blood for examination and a revolving slab to support the plate and wherein a ray of light is passed from below through an opening in the round portion of the plate and is detected by a photoelectric call located above the source sending out the light.

U.S. Pat. No. 3,302,452 deals with a device equipped with optical measurement means able to pass a ray of light through a test tube holding plasma and reagent and revolving around its own lengthwise axis, which is sloped at an angle of between 85° and 70° to the line of measurement. The test tubes are conveyed individually with conveyor means through a plurality of control stations before arriving for measurement.

DE-OS Pat. No. 2408214 shows a photometer using a ray of filtered and concentrated light.

U.S. Pat. No. 3,905,769 employs monochromatic light in the form of a laser beam.

U.S. Pat. No. 3,969,079 proposes a very complicated device using one single source of light to illuminate two test tubes so as to conduct two separate examinations at one and the same time, one photosensor being used for each test tube.

U.S. Pat. No. 4,125,327 discloses a device able to carry out an examination of a plurality of test tubes stirred with means introduced into the test tubes themselves.

GB Pat. No. 1,270,416 discloses a device wherein the test tube together with optical measurement means is oscillated around a horizontal axis.

U.S. Pat. No. 3,450,501 and DE-OS No. 2,413,285 comprise devices wherein the ray of light passes along the lengthwise axis of the test tube and is detected by the sensor means (in U.S. Pat. No. 3,450,501) and by the naked eye of the observer (in DE-OS) at a point pre-disposed sideways to the lengthwise axis of the test tube.

In DE-OS No. 2413285 the ray is oriented towards the observer with mirrors and is concentrated with several lenses.

One drawback of the known devices is that they have an optical geometry which does not make possible a linear ratio between the true opacity of the sample and the optical density detected, this being a fact which makes it hard to determine the true characteristics of the phenomenon being investigated.

Another drawback lies in the fact that the known systems require a fresh calibration each time that a change in optical density takes place.

The present invention aims to overcome those drawbacks.

Another purpose of the invention is to provide an accurate examination of several samples of plasma at a very fast rate in an automatic or semi-automatic way.

A further purpose of the invention is to minimize dispersion of light by embodying an optimum optical geometry that enables white light belonging to the visible range of the spectrum and an inexpensive photosensor to be employed.

The invention is therefore embodied in an indicator device to study the phenomena of blood coagulation, concentration and aggregation of blood platelets and the like which includes:

support means bearing test tubes equipped in a plurality of upright hollows provided with very narrow cross-wise through holes, conveyor means and withdrawal means for the support means to and from an indicator station provided with loading and discharging means and including means generating light, photosensor means, stirring means and thermostat heating means characterized by the fact that the indicator station comprises a lengthwise lodgement for the support means bearing test tubes, whereby the lodgement is equipped with a plurality of holes to convey optical rays and the holes correspond in number, position and advantageously also in diameter to the plurality of the crosswise holes provided in the support means bearing test tubes positioned in an intermediate position in relation to the conveying holes, whereby possible suitable electronic means also coordinate and regulate the working of the conveyor, withdrawal and loading/discharging means and of means to inject reagents with reference to the photoindicator means.

The optimum optical geometry of this invention has been determined on the basis of experiments and tests.

Other details and features of the invention will stand out from the description given below by way of non-limitative example and with reference to the accompanying drawings, in which.

In the figures the same parts or parts having the same functions bear the same reference numbers.

Figure 1:
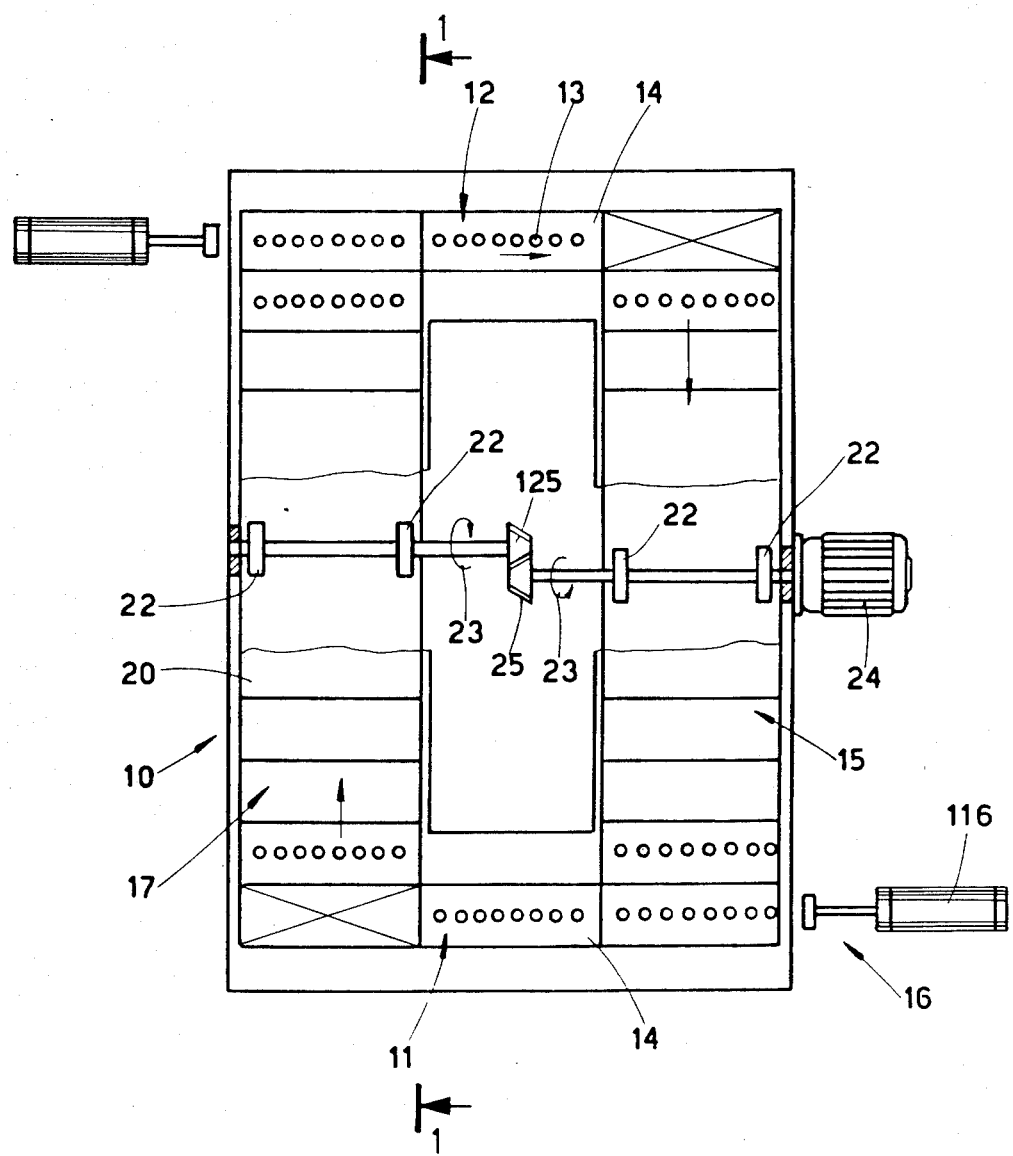
FIG. 1 illustrates a plan view of the invention.

In FIG. 1 the reference 10 indicates the device which is the subject of the invention and wherein are an indicator station 11 pre-arranged on the front side of the device, a station 12 for loading the test tubes 13 into the means 14 bearing the test tubes 13. Means 15 convey the means 14 bearing test tubes to the indicator station 11. The loading/discharging means 16 are pre-disposed upstream from the conveyor means 15 and able to load or discharge from the indicator station 11 as will be described hereinafter. The withdrawal means 17 are pre-arranged downstream from the indicator station 11 and able to withdraw the means 14 bearing test tubes as they leave the station 11.

Figure 2:
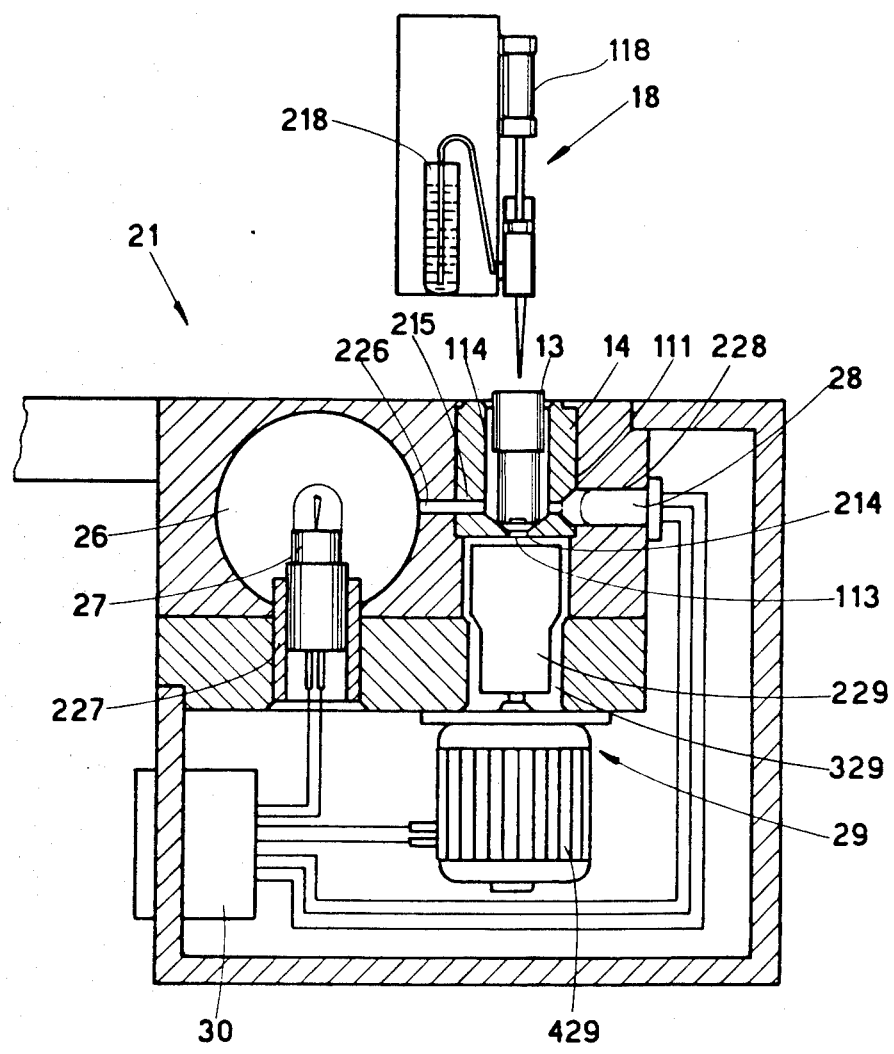
FIG. 2 illustrates a lengthwise section of the indicator station of the invention.

FIG. 2 also shows the injector means for reagants 18 pre-arranged above the indicator station 11.

According to the invention the means 14 bearing test tubes consist of a rectangular block 14 comprising a plurality of upright hollows 114 having through holes 214 in their bottom.

The block 14 also comprises crosswise holes 215 passing through each hollow and pre-disposed at a predetermined height.

Said holes 215 have a narrow diameter of between 1.5 and 2.5 mm., preferably 2 mm., and the diameter of the hollows 114 ranges from 7 to 8 mm. and is preferably 7.5 mm., which corresponds to an optimum optical distance.

The means 14 bearing test tubes can be inserted from the side into the groove 111 provided for in the indicator station 11 by means of the loading/discharging means 16, which consist of a pusher means 116 of any desired type, here being a pneumatic piston pre-arranged parallel to the lengthwise axis of the groove 111.

Figure 3:
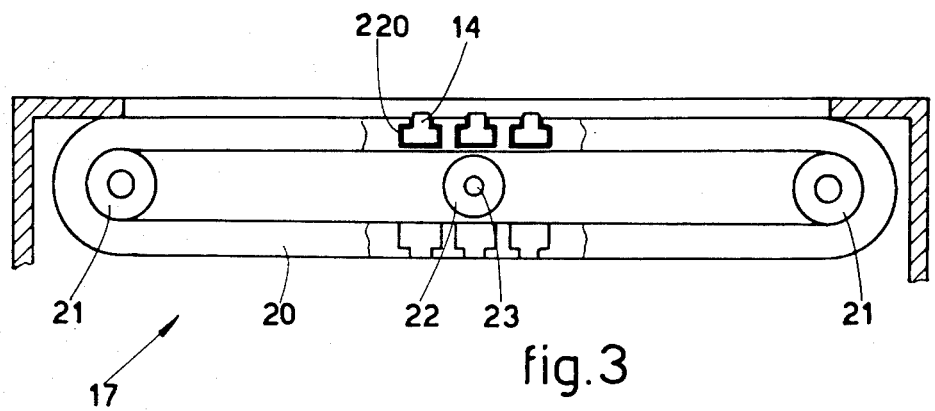
FIG. 3 illustrates a partial lengthwise section of the means conveying the means bearing test tubes taken alongline 3—3 of FIG. 1.

With reference to FIG. 3 the conveyor means 15 and withdrawal means 17 are substantially alike and consist of a conveyor belt 20 made of a flexible material and rotating on a plurality of guide pulleys 21 and driven by a powered pulley 22 keyed to a drive shaft 23.

The conveyor belt 20 too is equipped with crosswise hollows 220 pre-arranged on its outer surface and able to accept the means 14 bearing test tubes by sideways insertion.

So as to obtain a coordinated step-by-step movement of the conveyor 15 and withdrawal means 17 in their respective directions of forward displacement, a step motor 24 is used which drives the propelling shaft 23 of the conveyor means 15 in one direction, while the propelling shaft 23 of the withdrawal means 17 is moved in the opposite direction by the coupling with gear wheels 25, 125.

In this way there is an opposite and coordinated movement of the two carrying means 15 and 17, the step of their forward movement being the same as the width of the means 14 bearing test tubes.

According to the invention the withdrawal means 17 too are equipped at their end with loading means 16 like those already described and able to load the means 14 bearing test tubes at the station 12 where the test tubes 13 are loaded.

Furthermore, the indicator station 11 comprises a plurality of chambers 26 which are advantageously spherical and contain a light bulb 27 lodged in a holder 227 at the middle of each chamber 26 so as to correspond with a guide hole 226 that communicates with the relative crosswise hole 215 provided in the means 14 bearing test tubes.

The indicator station 11 also includes a plurality of suitable electrical photosensor means 28 of a known type positioned within the holes 228 which are pre-disposed on the same axis as the guide holes 226 located on the opposite side of the groove 111.

According to the invention the distance between the photosensor means 28 and the center of the test tubes 13 can be adjusted advantageously during the calibration phase so as to regulate the ratio between the optical density of the test tubes 13 as received by the photosensor means 28 and the electrical signal emitted as output by the means 28.

Stirring means 29 are located beneath each test tube and consist of a magnetic cylinder 229 arranged in a hollow 329 on the drive shaft of a small motor 429 secured to the structure of the indicator station 11.

Whenever the small motor 429 is set in rotation, the magnetic cylinder 229 stirs the plasma inside the relative test tube by causing a small magnetic plate 113 immersed in the plasma to revolve.

The electrical wires to supply current to the light bulbs 27 and small electric motors 429 and also the wires conveying the signals from the photosensor means 28 are connected to a connection block 30, which in turn can be coupled to possible governing and regulating means which are not shown here but which arrange for the overall coordination of the working of the device and for cooperation with possible peripheral means such as printing means, display means or the like.

It is timely for us to emphasise that the operations of the loading/discharging means 16 and injector means 18 are coordinated with and embodied in the overall working of the device.

For this purpose the pusher means can comprise valves able to govern the pneumatic piston 116, and also dosing means 118 of the injector means 18 can have valves suitable for regulating their injection of the reagents held in the receptacles 218.

This invention also includes known thermostatic means to keep the temperature at 37° C. The thermostatic means are not shown herein.

We have described here a preferential embodiment of the invention, but other variants are possible.

Thus the shapes, proportions and sizes can be varied. It is possible to utilize any source of light or any photosensor means to receive the light. It is possible to utilize thermostatic means for each test tube 13 or for each whole block 14 bearing test tubes or for the whole device. All of the above is possible for a technician in this field without going beyond the scope of the invention.

We claim:

1. Indicator device for studying the phenomena of blood coagulation, concentration and aggregation of blood platelets including:

an indicator station defining a lengthwise groove, a plurality of spaced coaxial holes extending crosswise of said groove, a light positioned on a line coaxially extending from each end of a hole on one side of said groove, a photosensor means positioned in an end of each hole on the other side of said groove, a support means defining a plurality of parallel upright hollows for bearing test tubes slidable within said groove and defining coaxial crosswise holes communicating with said hollows and coaxially corresponding to said holes extending crosswise of said groove, said support means also defining holes in the bottoms of said hollows, a conveyor to move said support means to and from said indicator station, loading and discharge means to insert into and remove said support means from said groove, stirring means positioned below each hole in the bottom of each hollow and an injector positioned above said support for loading said test tubes.

2. The device as in claim 1 wherein said indicator station further defined a substantially closed chamber for said light.

3. The device as in claim 2 wherein said chamber is substantially spherical.

4. The device as in claims 1, 2 or 3 wherein said photosensor means is longitudinally positionable within the hole.

5. The device as in claims 1, 2 or 3 including means to coordinate and regulate the working of the conveyor means, the loading and discharge means and injector.

* * * * *